US007566705B2

(12) United States Patent
Hassan et al.

(10) Patent No.: US 7,566,705 B2
(45) **Date of Patent: *Jul. 28, 2009**

(54) COMBINATION OF FORMOTEROL AND MOMETASONE FUROATE FOR ASTHMA

(75) Inventors: Ian F Hassan, Morris Plains, NJ (US); Jeremy G Clarke, Bath (GB); Henry L Danahay, Horsham (GB)

(73) Assignee: Novartis AG, Basel (CH)

( * ) Notice: Subject to any disclaimer, the term of this patent is extended or adjusted under 35 U.S.C. 154(b) by 68 days.

This patent is subject to a terminal disclaimer.

(21) Appl. No.: 11/199,291

(22) Filed: Aug. 8, 2005

(65) Prior Publication Data

US 2006/0009437 A1 Jan. 12, 2006

Related U.S. Application Data

(63) Continuation of application No. 10/718,316, filed on Nov. 20, 2003, now Pat. No. 7,067,502, which is a continuation of application No. 10/262,408, filed on Oct. 1, 2002, now abandoned, which is a continuation of application No. 09/942,805, filed on Aug. 30, 2001, now abandoned, which is a continuation of application No. PCT/EP00/01722, filed on Mar. 1, 2000.

(30) Foreign Application Priority Data

Mar. 3, 1999 (GB) ................................ 9904919.9

(51) Int. Cl.
*A61K 31/56* (2006.01)
*A61K 31/135* (2006.01)

(52) U.S. Cl. ...................................... 514/181; 514/653

(58) Field of Classification Search ................. 514/181, 514/653

See application file for complete search history.

(56) References Cited

U.S. PATENT DOCUMENTS

| | | | | |
|---|---|---|---|---|
| 5,837,699 | A | 11/1998 | Sequeira et al. | 514/169 |
| 5,874,063 | A | 2/1999 | Briggner et al. | 424/45 |
| 6,030,604 | A | 2/2000 | Trofast | 424/46 |
| 7,067,502 | B2 * | 6/2006 | Hassan et al. | 514/181 |

FOREIGN PATENT DOCUMENTS

| | | |
|---|---|---|
| EP | 416951 | 3/1992 |
| EP | 0 642 992 | 3/1995 |
| WO | 93/11773 | 6/1993 |
| WO | 95/05805 | 3/1995 |
| WO | 95/20393 | 8/1995 |
| WO | 96/19198 | 6/1996 |
| WO | 98/34595 | 8/1998 |
| WO | 98/41193 | 9/1998 |
| WO | 99/18971 | 4/1999 |
| WO | 00/15234 | 3/2000 |

OTHER PUBLICATIONS

Barnes, "Efficacy of Inhaled Corticosteroids in Asthma", J. Allergy Clin. Immunol., vol. 102, No. 4, Part 1, pp. 531-538 (1998).

Dal Negro et al., "Chronic Airways Obstruction—Responsiveness to Combined, Pressurized Salbutamol-Beclomethasone Diproplonate (Ventolin Flogo*)", Clin Trials J., vol. 20, No. 6, pp. 366-372 (1983).

Gennaro (Eds.) et al., Remington's Pharmaceutical Sciences, 18$^{th}$ Edition, pp. 1699-1701 and pp. 1706-1707 (1990).

Lipworth et al., "Effects of Treatment with Formoterol on Bronchoprotection Against Methacholine", Am. J. Med., vol. 104, pp. 431-438 (1998).

O'Connor, "Combination Therapy", Pulmonary Pharmacology & Therapeutics, vol. 11, pp. 397-399 (1998).

Pauwels et al., "Effect of Inhaled Formoterol and Budesonide on Exacerbations of Asthma", N. Engl. J. Med., vol. 337, No. 20, pp. 1405-1411 (1997).

Jean H. Marsac et al, "Inhaled beta Adrenaergic Agonists and Inhaled Steroids in Treatment of Asthma," Annals of Allergy, vol. 63, pp. 220-224 (1989).

Svedmyr Nils, "The Current Place of beta-2-agonists in the Management of Asthma", Lung, pp. 105-110 (1990).

Kia Soong Tan et al, "Systemic Corticosteroids Rapidly Reverses Bronchodilator Sub-sensitivity Induced by Formoterol in Asthmatic Patients," American Journal of Respiratory and Critical Care Medicine, vol. 156, pp. 28-35 (1997).

J. O. Warner et al, "Third International Consensus Statement on the Management of Childhood Asthma," Pediatric Pulmonology Consensus Statement: Asthma Management, No. 212, pp. 1-17 (1998).

Benemar Guimaraes et al, Brazilian Consensus in the Management of Asthma: Fortaleza, CE, pp. 1-64 (1994).

Juan Jose L. Sienra-Monge et al., "Asthma", Salud publica Mex, vol. 41, No. 1,I Guernavaca (1999).

P. J. Wilding et al., "Interaction between corticosteroids and beta-agonists in asthma," Monaldi Arch Chest Dis, vol. 51:1, pp. 39-41 (1996).

U.S. Department of Health & Human Services, Practical Guide for the Diagnosis and Management of Asthma, NIH Publication No. 97-4053, Oct. 1997.

M. C. Berenbaum, Synergy, additivism and antagonism in immunosuppression—a critical review Clin. exp. Immunol, vol. 28, pp. 1-18 (1977).

A. Grimfield et al., "Place of the inhaled therapies in the approach to childhood asthma,"pp. 1-5 (1992).

LIBBS Farmaceutica Ltda., Supportive Information for the Technical Examination, pp. 1-18 (Jun. 2004 and Mar. 2007).

LIBBS Farmaceutica Ltda., Priority Examination, pp. 1-2 (May 2007).

* cited by examiner

*Primary Examiner*—San-ming Hui
(74) *Attorney, Agent, or Firm*—Leslie Fischer; Jennifer C. Chapman

(57) ABSTRACT

A medicament containing, separately or together, (A) formoterol or a pharmaceutically acceptable salt thereof or a solvate of formoterol or a solvate of the salt and (B) mometasone furoate, for simultaneous, sequential or separate administration in the treatment of an inflammatory or obstructive airways disease.

20 Claims, No Drawings

COMBINATION OF FORMOTEROL AND MOMETASONE FUROATE FOR ASTHMA

This application is a continuation of U.S. patent application Ser. No. 10/718,316, filed Nov. 20, 2003, which is a continuation of U.S. patent application Ser. No. 10/262,408, filed Oct. 1, 2002, which is a continuation of U.S. patent application Ser. No. 09/942,805, filed Aug. 30, 2001, now abandoned, which is a continuation of PCT Patent Application No. PCT/EP00/01722, filed Mar. 1, 2000, which in their entirety are herein incorporated by reference.

This invention relates to combinations of a beta-2 agonist and a steroid and their use for the treatment of inflammatory or obstructive airways diseases.

Formoterol, N-[2-hydroxy-5-(1-hydroxy-2-((2-(4-methoxyphenyl)-1-methylethyl)amino)-ethyl)phenyl]formamide, particularly in the form of its fumarate salt, is a bronchodilator used in the treatment of inflammatory or obstructive airways diseases. Mometasone furoate, (11β,16α)-9,21-dichloro-17-[(2-furanylcarbonyl)oxy]-11-hydroxy-16-methylpregna-1,4-diene-3,20-dione, alternatively designated 9α,21-dichloro-16α-methyl-1,4-pregnadiene-11β,17α-diol-3,20-dione 17-(2'-furoate), is a topical anti-inflammatory corticosteroid which is described in U.S. Pat. No. 4,472,393.

It has now surprisingly been found that a significant unexpected therapeutic benefit, particularly a synergistic therapeutic benefit, in the treatment of inflammatory or obstructive airways diseases can be obtained by combination therapy using formoterol, in free form or in the form of a salt or solvate thereof, and mometasone furoate. For instance, it is possible using this combination therapy to reduce the dosages of mometasone furoate or formoterol required for a given therapeutic effect considerably compared with those required using treatment with mometasone furoate or formoterol alone, thereby minimising possibly undesirable side effects. In particular, it has been found that these combinations, particularly as compositions containing formoterol and mometasone furoate, induce an anti-inflammatory activity which is significantly greater than that induced by formoterol or mometasone furoate alone and that the amount of mometasone furoate needed for a given anti-inflammatory effect may be significantly reduced when used in admixture with formoterol, thereby reducing the risk of undesirable side effects from the repeated exposure to the steroid involved in the treatment of inflammatory or obstructive airways diseases.

Furthermore, using the combination therapy of the invention, particularly using compositions containing formoterol and mometasone furoate, medicaments which have a rapid onset of action and a long duration of action may be prepared. Moreover, using such combination therapy, medicaments which result in a significant improvement in lung function may be prepared. In another aspect, using the combination therapy of the invention, medicaments which provide improved control of obstructive or inflammatory airways diseases, or a reduction in exacerbations of such diseases, may be prepared. In a further aspect, using compositions of the invention, medicaments which can be used on demand in rescue treatment of obstructive or inflammatory airways diseases, or which reduce or eliminate the need for treatment with short-acting rescue medicaments such as salbutamol or terbutaline, may be prepared; thus medicaments based on compositions of the invention facilitate the treatment of an obstructive or inflammatory airways disease with a single medicament.

In one aspect, the present invention provides a medicament containing, separately or together, (A) formoterol or a pharmaceutically acceptable salt thereof or a solvate of formoterol or a solvate of said salt and (B) mometasone furoate, for simultaneous, sequential or separate administration in the treatment of an inflammatory or obstructive airways disease.

In another aspect, the present invention provides a method of treating an inflammatory or obstructive airways disease which comprises administering to a subject in need of such treatment effective amounts of (A) as hereinbefore defined and (B) as hereinbefore defined.

In a further aspect, the present invention provides a phamaceutical composition comprising a mixture of effective amounts of (A) as hereinbefore defined and (B) as hereinbefore defined, optionally together with a pharmaceutically acceptable carrier.

The present invention also provides (A) and (B) as hereinbefore defined for use in combination therapy by simultaneous, sequential or separate administration in the treatment of an inflammatory or obstructive airways disease.

The invention further provides the use of (A) as hereinbefore defined or (B) as hereinbefore defined in the preparation of a medicament for combination therapy by simultaneous, sequential or separate administration of (A) and (B) in the treatment of an inflammatory or obstructive airways disease.

In a yet further aspect, the present invention provides a pharmaceutical composition for use in the treatment of an inflammatory or obstructive airways disease comprising (A) and (B) as hereinbefore defined.

The present invention still further provides the use of (A) and (B) as hereinbefore defined for the preparation of a medicament for combination therapy by simultaneous, sequential or separate administration in the treatment of an inflammatory or obstructive airways disease.

Pharmaceutically acceptable salts of formoterol include, for example, salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic and 3-hydroxy-2-naphthalene carboxylic acids.

Component (A) may be in any isomeric form or mixture of isomeric forms, for example a pure enantiomer, a mixture of enantiomers, a racemate or a mixture thereof. It may be in the form of a solvate, for example a hydrate, thereof, for example as described in U.S. Pat. No. 3,994,974 or U.S. Pat. No. 5,684,199, and may be present in a particular crystalline form, for example as described in WO95/05805. Preferably, component (A) is formoterol fumarate, especially in the form of the dihydrate.

Administration of the medicament or pharmaceutical composition as hereinbefore described, i.e. with (A) and (B) in admixture or separate, is preferably by inhalation, i.e. (A) and (B) or the mixture thereof are in inhalable form. The inhalable form of the medicament i.e. of (A) and/or (B) may be, for example, an atomizable composition such as an aerosol comprising the active ingredient, i.e. (A) and (B) separately or in admixture, in solution or dispersion in a propellant, or a nebulizable composition comprising a dispersion of the active ingredient in an aqueous, organic or aqueous/organic medium. For example, the inhalable form of the medicament may be an aerosol comprising a mixture of (A) and (B) in solution or dispersion in a propellant, or a combination of an aerosol containing (A) in solution or dispersion in a propellant with an aerosol containing (B) in solution or dispersion in a propellant. In another example, the inhalable form is a nebulizable composition comprising a dispersion of (A) and (B) in an aqueous, organic or aqueous/organic medium, or a combination of a dispersion of (A) in such a medium with a dispersion of (B) in such a medium.

An aerosol composition suitable for use as the inhalable form of the medicament may comprise the active ingredient in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example fluorine-substituted methanes, ethanes, propanes, butanes, cyclopropanes or cyclobutanes, particularly 1,1,1,2-tetrafluoroethane (HFA134a) and 1,1,1,2,3,3,3-heptafluoropropane (HFA227), or mixtures of two or more such halogen-substituted hydrocarbons. Where the active ingredient is present in suspension in the propellant, i.e. where it is present in particulate form dispersed in the propellant, the aerosol composition may also contain a lubricant and a surfactant, which may be chosen from those lubricants and surfactants known in the art. Other suitable aerosol compositions include surfactant-free or substantially surfactant-free aerosol compositions. The aerosol composition may contain up to about 5% by weight, for example 0.002 to 5%, 0.01 to 3%, 0.015 to 2%, 0.1 to 2%, 0.5 to 2% or 0.5 to 1%, by weight of the active ingredient, based on the weight of the propellant. Where present, the lubricant and surfactant may be in an amount up to 5% and 0.5% respectively by weight of the aerosol composition. The aerosol composition may also contain a co-solvent such as ethanol in an amount up to 30% by weight of the composition, particularly for administration from a pressurised metered dose inhalation device.

In another embodiment of the invention, the inhalable form is a dry powder, i.e. (A) and/or (B) are present in a dry powder comprising finely divided (A) and/or (B) optionally together with a finely divided pharmaceutically acceptable carrier, which is preferably present and may be one or more materials known as pharmaceutically acceptable carriers, preferably chosen from materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran or mannitol. An especially preferred carrier is lactose. The dry powder may be in capsules of gelatin or plastic, or in blisters, for use in a dry powder inhalation device, preferably in dosage units of (A) and/or (B) together with the carrier in amounts to bring the total weight of powder per capsule to from 5 mg to 50 mg. Alternatively, the dry powder may be contained as a reservoir in a multi-dose dry powder inhalation device.

In the finely divided particulate form of the medicament, and in the aerosol composition where the active ingredient is present in particulate form, the active ingredient may have an average particle diameter of up to about 10 μm, for example 0.1 to 5 μm, preferably 1 to 5 μm. The solid carrier, where present, generally has a maximum particle diameter up to 300 μm, preferably up to 212 μm, and conveniently has a mean particle diameter of 40 to 100 μm, e.g. 50 to 75 μm. The particle size of the active ingredient, and that of a solid carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The inhalable medicament may be administered using an inhalation device suitable for the inhalable form, such devices being well known in the art. Accordingly, the invention also provides a pharmaceutical product comprising a medicament or pharmaceutical composition as hereinbefore described in inhalable form as hereinbefore described in association with one or more inhalation devices. In a further aspect, the invention provides an inhalation device, or a pack of two or more inhalation devices, containing a medicament or pharmaceutical composition as hereinbefore described in inhalable form as hereinbefore described.

Where the inhalable form of the active ingredient is an aerosol composition, the inhalation device may be an aerosol vial provided with a valve adapted to deliver a metered dose, such as 10 to 100 μl, e.g. 25 to 50 μl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, for example an electronically controlled device such as an AERx (ex Aradigm, US) or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. Suitable such dry powder inhalation devices are well known. For example, a suitable device for delivery of dry powder in encapsulated form is that described in U.S. Pat. No. 3,991,761, while a suitable MDPI device is that described in WO97/20589.

The medicament of the invention is preferably a pharmaceutical composition comprising a mixture of (A) as hereinbefore defined and (B) as hereinbefore defined, preferably together with a pharmaceutically acceptable carrier as hereinbefore described.

The weight ratio of formoterol, or salt or solvate thereof, to mometasone furoate may be, in general, from 2:1 to 1:2000, for example from 1:1 to 1:1000, from 1:2 to 1:100, or from 1:5 to 1:50. More usually, this ratio is from 1:10 to 1:25, for example from 1:15 to 1:25. The two drugs may be administered separately in the same ratio. Specific examples of this ratio, to the nearest whole number, include 1:10, 1:11, 1:12, 1:13, 1:14, 1:15, 1:16, 1:17, 1:18, 1:19, 1:20, 1:21, 1:22, 1:23, 1:24 and 1:25. The above weight ratios apply particularly where (A) is formoterol fumarate dihydrate. Thus, since the molecular weights of formoterol fumarate dihydrate and mometasone furoate are 840.9 and 521.4 respectively, the corresponding molar ratios of (A) to (B) may be, in general, from 1.24:1 to 1:3227, for example from 0.62:1 to 1:1613, from 1:3.2 to 1:161, or from 1:8.1 to 1:80.7; more usually from 1:16.1 to 1:40.3, for example from 1:24.2 to 1:40.3; specific examples of the molar ratio being 1:16.1, 1:17.8, 1:19.4, 1:21, 1:22.6, 1:24.2, 1:25.8, 1:27.4, 1:29, 1:30.7, 1:32.3, 1:33.9, 1:35.5, 1:37.1, 1:38.7 and 1:40.3.

A suitable daily dose of formoterol, or salt or solvate thereof, particularly as formoterol fumarate dihydrate, for inhalation may be from 1 to 72 μg, for example from 1 to 60

μg, generally from 3 to 50 μg, preferably from 6 to 48 μg, for instance from 6 to 24 μg. A suitable daily dose of mometasone furoate for inhalation may be from 50 to 2000 μg, for example from 100 to 2000 μg, from 100 to 1600 μg, from 100 to 1000 μg, or from 100 to 800 μg, preferably from 200 to 500 μg, for instance from 200 to 400 μg. The precise dose used will of course depend on the condition to be treated, the patient and the efficiency of the inhalation device.

A suitable unit dose of formoterol component (A), particularly as formoterol fumarate dihydrate, may be from 1 to 72 μg, for example from 1 to 60 μg, generally from 3 to 48 μg, preferably from 6 to 36 μg, especially from 12 to 24 μg. A suitable unit dose of mometasone furoate (B) may be from 25 μg to 2000 μg, for example from 50 μg to 1000 μg, preferably from 500 μg to 800 μg, more preferably from 100 μg to 500 μg, especially from 100 to 400 μg, e.g. from 200 to 400 μg. These unit doses may suitably be administered once or twice daily in accordance with the suitable daily dose mentioned hereinbefore. For on demand usage, a dosage unit containing 6 μg or 12 μg of (A) and 50 μg or 100 μg of mometasone furoate (B) is preferred.

In one preferred embodiment of the invention, the medicament of the invention is a pharmaceutical composition which is a dry powder in a capsule containing a unit dose of (A) and (B), for example for inhalation from a single capsule inhaler, the capsule suitably containing, where (A) is formoterol fumarate dihydrate, from 3 μg to 36 μg of (A), preferably from 6 μg to 24 μg of (A), especially from 12 μg to 24 μg of (A), and from 25 μg to 800 μg, e.g. 25 μg to 500 μg or 25 μg to 400 μg, of (B), preferably from 50 μg to 400 μg. of (B), especially from 100 to 400 μg of (B), together with a pharmaceutically acceptable carrier as hereinbefore described in an amount to bring the total weight of dry powder per capsule to between 5 mg and 50 mg, for example 5 mg, 10 mg, 15 mg, 20 mg, 25 mg, 30 mg, 35 mg, 40 mg, 45 mg or 50 mg, preferably 20 to 25 mg, especially 25 mg.

In another preferred embodiment of the invention, the medicament of the invention is a pharmaceutical composition which is a dry powder for administration from a reservoir of a multi-dose dry powder inhaler adapted to deliver 3 mg to 25 mg of powder containing a unit dose of (A) and (B) per actuation, for example, where (A) is formoterol fumarate dihydrate, a powder comprising, by weight, 3 to 36 parts, preferably 6 to 24 parts, especially 12 to 24 parts of (A); 25 to 800 parts, e.g. 25 to 500 parts, preferably 50 to 400 parts, especially 100 to 400 parts of (B); and 2164 to 24972 parts, preferably 4164 to 14972 parts, especially 4164 to 9972 parts of a pharmaceutically acceptable carrier as hereinbefore described.

In accordance with the above, the invention also provides a pharmaceutical kit comprising (A) and (B) as hereinbefore defined in separate unit dosage forms, said forms being suitable for administration of (A) and (B) in effective amounts. Such a kit suitably further comprises one or more inhalation devices for administration of (A) and (B). For example, the kit may comprise one or more dry powder inhalation devices adapted to deliver dry powder from a capsule, together with capsules containing a dry powder comprising a dosage unit of (A) and capsules containing a dry powder comprising a dosage unit of (B). In another example, the kit may comprise a multidose dry powder inhalation device containing in the reservoir thereof a dry powder comprising (A) and a multidose dry powder inhalaiton device containing in the reservoir thereof a dry powder comprising (B). In a further example, the kit may comprise a metered dose inhaler containing an aerosol comprising comprising (A) in a propellant and a metered dose inhaler containing an aerosol comprising (B) in a propellant.

Treatment of inflammatory or obstructive airways diseases in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis and emphysema, bronchiectasis and exacerbation of airways hyperreactivity consequent to other drug therapy, in particular other inhaled drug therapy. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

The invention is illustrated by the following Examples, in which parts are by weight unless stated otherwise.

EXAMPLE 1

Aerosol Composition for Metered Dose Inhaler

| Ingredient | % by weight |
|---|---|
| Formoterol fumarate dihydrate | 0.012 |
| Mometasone furoate | 0.250 |
| Ethanol (absolute) | 2.500 |
| HFA 227 | 60.768 |
| HFA 134a | 36.470 |

EXAMPLE 2

Dry Powder

| Ingredient | % by weight |
|---|---|
| Formoterol fumarate dihydrate | 0.048 |
| Mometasone furoate | 1.000 |
| Lactose monohydrate | 98.952 |

EXAMPLE 3

A dry powder suitable for delivery from the reservoir of the multi-dose inhaler described in WO97/20589 is prepared by mixing 12 parts of formoterol fumarate dihydrate which has been ground to a mean particle diameter of 1-5 μm in an air-jet mill, 250 parts of mometasone furoate which has been similarly ground to a mean particle diameter of 1-5 μm and 4738 parts of lactose monohydrate having a particle diameter below 212 μm.

EXAMPLES 4-92

Example 3 is repeated, but using the amounts of the ingredients shown in the table below in place of the amounts used in that Example:

| Example | Formoterol Fumarate Dihydrate (Parts) | Mometasone Furoate (Parts) | Lactose Monohydrate (Parts) |
|---|---|---|---|
| 4 | 12 | 50 | 4938 |
| 5 | 12 | 100 | 4888 |
| 6 | 12 | 150 | 4838 |
| 7 | 12 | 200 | 4788 |
| 8 | 6 | 50 | 4944 |
| 9 | 6 | 100 | 4894 |
| 10 | 6 | 150 | 4844 |
| 11 | 6 | 200 | 4794 |
| 12 | 6 | 250 | 4744 |
| 13 | 18 | 50 | 4932 |
| 14 | 18 | 100 | 4882 |
| 15 | 18 | 150 | 4832 |
| 16 | 18 | 200 | 4782 |
| 17 | 18 | 250 | 4732 |
| 18 | 24 | 50 | 4926 |
| 19 | 24 | 100 | 4876 |
| 20 | 24 | 150 | 4826 |
| 21 | 24 | 200 | 4776 |
| 22 | 24 | 250 | 4726 |
| 23 | 30 | 50 | 4920 |
| 24 | 30 | 100 | 4870 |
| 25 | 30 | 150 | 4820 |
| 26 | 30 | 200 | 4770 |
| 27 | 30 | 250 | 4720 |
| 28 | 36 | 50 | 4914 |
| 29 | 36 | 100 | 4864 |
| 30 | 36 | 150 | 4814 |
| 31 | 36 | 200 | 4764 |
| 32 | 36 | 250 | 4714 |
| 33 | 6 | 50 | 9944 |
| 34 | 6 | 100 | 9894 |
| 35 | 6 | 150 | 9844 |
| 36 | 6 | 200 | 9794 |
| 37 | 6 | 250 | 9744 |
| 38 | 12 | 50 | 9938 |
| 39 | 12 | 100 | 9888 |
| 40 | 12 | 150 | 9838 |
| 41 | 12 | 200 | 9788 |
| 42 | 12 | 250 | 9738 |
| 43 | 18 | 50 | 9932 |
| 44 | 18 | 100 | 9882 |
| 45 | 18 | 150 | 9832 |
| 46 | 18 | 200 | 9782 |
| 47 | 18 | 250 | 9732 |
| 48 | 24 | 50 | 9926 |
| 49 | 24 | 100 | 9876 |
| 50 | 24 | 150 | 9826 |
| 51 | 24 | 200 | 9776 |
| 52 | 24 | 250 | 9726 |
| 53 | 30 | 50 | 9920 |
| 54 | 30 | 100 | 9870 |
| 55 | 30 | 150 | 9820 |
| 56 | 30 | 200 | 9770 |
| 57 | 30 | 250 | 9720 |
| 58 | 36 | 50 | 9914 |
| 59 | 36 | 100 | 9864 |
| 60 | 36 | 150 | 9814 |
| 61 | 36 | 200 | 9764 |
| 62 | 36 | 250 | 9714 |
| 63 | 6 | 50 | 14944 |
| 64 | 6 | 100 | 14894 |
| 65 | 6 | 150 | 14844 |
| 66 | 6 | 200 | 14794 |
| 67 | 6 | 250 | 14744 |
| 68 | 12 | 50 | 14938 |
| 69 | 12 | 100 | 14888 |
| 70 | 12 | 150 | 14838 |
| 71 | 12 | 200 | 14788 |
| 72 | 12 | 250 | 14738 |
| 73 | 18 | 50 | 14932 |
| 74 | 18 | 100 | 14882 |
| 75 | 18 | 150 | 14832 |
| 76 | 18 | 200 | 14782 |
| 77 | 18 | 250 | 14732 |
| 78 | 24 | 50 | 14926 |
| 79 | 24 | 100 | 14876 |
| 80 | 24 | 150 | 14826 |
| 81 | 24 | 200 | 14776 |
| 82 | 24 | 250 | 14726 |
| 83 | 30 | 50 | 14920 |
| 84 | 30 | 100 | 14870 |
| 85 | 30 | 150 | 14820 |
| 86 | 30 | 200 | 14770 |
| 87 | 30 | 250 | 14720 |
| 88 | 36 | 50 | 14914 |
| 89 | 36 | 100 | 14864 |
| 90 | 36 | 150 | 14814 |
| 91 | 36 | 200 | 14764 |
| 92 | 36 | 250 | 14714 |

EXAMPLE 93

Gelatin capsules suitable for use in a capsule inhaler such as that described in U.S. Pat. No. 3,991,761 are prepared, each capsule containing a dry powder obtained by mixing 12 μg of formoterol fumarate dihydrate which has been ground to a mean particle diameter of 1 to 5 μm in an air jet mill, 250 μg of mometasone furoate which has been similarly ground to a mean particle diameter of 1 to 5 μm and 24738 μg of lactose monohydrate having a particle diameter below 212 μm.

EXAMPLES 94-152

Example 93 is repeated, but using the amounts of the ingredients shown in the table below in place of the amounts used in that Example:

| Example | Formoterol Fumarate Dihydrate (Parts) | Mometasone Furoate (Parts) | Lactose Monohydrate (Parts) |
|---|---|---|---|
| 94 | 12 | 50 | 24938 |
| 95 | 12 | 100 | 24888 |
| 96 | 12 | 150 | 24838 |
| 97 | 12 | 200 | 24788 |
| 98 | 6 | 50 | 24944 |
| 99 | 6 | 100 | 24894 |
| 100 | 6 | 150 | 24844 |
| 101 | 6 | 200 | 24794 |
| 102 | 6 | 250 | 24744 |
| 103 | 18 | 50 | 24932 |
| 104 | 18 | 100 | 24882 |
| 105 | 18 | 150 | 24832 |
| 106 | 18 | 200 | 24782 |
| 107 | 18 | 250 | 24732 |
| 108 | 24 | 50 | 24926 |
| 109 | 24 | 100 | 24876 |
| 110 | 24 | 150 | 24826 |
| 111 | 24 | 200 | 24776 |
| 112 | 24 | 250 | 24726 |
| 113 | 30 | 50 | 24920 |
| 114 | 30 | 100 | 24870 |
| 115 | 30 | 150 | 24820 |
| 116 | 30 | 200 | 24770 |
| 117 | 30 | 250 | 24720 |
| 118 | 36 | 50 | 24914 |
| 119 | 36 | 100 | 24864 |
| 120 | 36 | 150 | 24814 |
| 121 | 36 | 200 | 24764 |
| 122 | 36 | 250 | 24714 |
| 123 | 6 | 50 | 19944 |
| 124 | 6 | 100 | 19894 |
| 125 | 6 | 150 | 19844 |
| 126 | 6 | 200 | 19794 |
| 127 | 6 | 250 | 19744 |
| 128 | 12 | 50 | 19938 |
| 129 | 12 | 100 | 19888 |
| 130 | 12 | 150 | 19838 |
| 131 | 12 | 200 | 19788 |
| 132 | 12 | 250 | 19738 |
| 133 | 18 | 50 | 19932 |
| 134 | 18 | 100 | 19882 |
| 135 | 18 | 150 | 19832 |
| 136 | 18 | 200 | 19782 |
| 137 | 18 | 250 | 19732 |
| 138 | 24 | 50 | 19926 |
| 139 | 24 | 100 | 19876 |
| 140 | 24 | 150 | 19826 |
| 141 | 24 | 200 | 19776 |
| 142 | 24 | 250 | 19726 |
| 143 | 30 | 50 | 19920 |
| 144 | 30 | 100 | 19870 |
| 145 | 30 | 150 | 19820 |
| 146 | 30 | 200 | 19770 |
| 147 | 30 | 250 | 19720 |
| 148 | 36 | 50 | 19914 |
| 149 | 36 | 100 | 19864 |
| 150 | 36 | 150 | 19814 |
| 151 | 36 | 200 | 19764 |
| 152 | 36 | 250 | 19714 |

EXAMPLES 153-176

Example 3 is repeated, but using the amounts of the ingredients shown in the table below in place of the amounts used in that Example:

| Example | Formoterol Fumarate Dihydrate (Parts) | Mometasone Furoate (Parts) | Lactose Monohydrate (Parts) |
|---|---|---|---|
| 153 | 6 | 25 | 2969 |
| 154 | 6 | 50 | 2944 |
| 155 | 6 | 100 | 2894 |
| 156 | 6 | 150 | 2844 |
| 157 | 6 | 200 | 2794 |
| 158 | 6 | 250 | 2744 |
| 159 | 12 | 25 | 2963 |
| 160 | 12 | 50 | 2938 |
| 161 | 12 | 100 | 2888 |
| 162 | 12 | 150 | 2838 |
| 163 | 12 | 200 | 2788 |
| 164 | 12 | 250 | 2738 |
| 165 | 12 | 300 | 2638 |
| 166 | 12 | 350 | 2588 |
| 167 | 12 | 400 | 2538 |
| 168 | 24 | 25 | 2951 |
| 169 | 24 | 50 | 2926 |
| 170 | 24 | 100 | 2876 |
| 171 | 24 | 150 | 2826 |
| 172 | 24 | 200 | 2776 |
| 173 | 24 | 250 | 2726 |
| 174 | 24 | 300 | 2676 |
| 175 | 24 | 350 | 2626 |
| 176 | 24 | 400 | 2576 |

EXAMPLES 177-281

Example 93 is repeated, but using the amounts of the ingredients shown in the table below in place of the amounts used in that Example:

| Example | Formoterol Fumarate Dihydrate (μg) | Mometasone Furoate (μg) | Lactose Monohydrate (μg) |
|---|---|---|---|
| 177 | 6 | 25 | 14969 |
| 178 | 6 | 50 | 14944 |
| 179 | 6 | 100 | 14894 |
| 180 | 6 | 150 | 14844 |
| 181 | 6 | 200 | 14794 |
| 182 | 6 | 250 | 14744 |
| 183 | 6 | 300 | 14694 |
| 184 | 6 | 350 | 14644 |
| 185 | 6 | 400 | 14594 |
| 186 | 12 | 25 | 14963 |
| 187 | 12 | 50 | 14938 |
| 188 | 12 | 100 | 14888 |
| 189 | 12 | 150 | 14838 |
| 190 | 12 | 200 | 14788 |
| 191 | 12 | 250 | 14738 |
| 192 | 12 | 300 | 14688 |
| 193 | 12 | 350 | 14638 |
| 194 | 12 | 400 | 14588 |
| 195 | 12 | 500 | 14488 |
| 196 | 24 | 25 | 14951 |
| 197 | 24 | 50 | 14926 |
| 198 | 24 | 100 | 14876 |
| 199 | 24 | 150 | 14826 |
| 200 | 24 | 200 | 13876 |
| 201 | 24 | 250 | 13826 |
| 202 | 24 | 300 | 13776 |
| 203 | 6 | 25 | 9969 |
| 204 | 6 | 50 | 9944 |
| 205 | 6 | 100 | 9894 |
| 206 | 6 | 150 | 9844 |
| 207 | 6 | 200 | 9794 |
| 208 | 6 | 250 | 9744 |
| 209 | 6 | 300 | 9694 |
| 210 | 12 | 25 | 9963 |

-continued

| Example | Formoterol Fumarate Dihydrate (μg) | Mometasone Furoate (μg) | Lactose Monohydrate (μg) |
|---|---|---|---|
| 211 | 12 | 50 | 9938 |
| 212 | 12 | 100 | 9888 |
| 213 | 12 | 150 | 9838 |
| 214 | 12 | 200 | 9788 |
| 215 | 12 | 250 | 9738 |
| 216 | 12 | 300 | 9688 |
| 217 | 12 | 400 | 9588 |
| 218 | 12 | 500 | 9488 |
| 219 | 24 | 25 | 9951 |
| 220 | 24 | 50 | 9926 |
| 221 | 24 | 100 | 9876 |
| 222 | 24 | 150 | 9826 |
| 223 | 24 | 200 | 9776 |
| 224 | 24 | 250 | 9726 |
| 225 | 24 | 300 | 9676 |
| 226 | 24 | 400 | 9576 |
| 227 | 24 | 500 | 9476 |
| 228 | 6 | 25 | 4969 |
| 229 | 6 | 50 | 4944 |
| 230 | 6 | 100 | 4894 |
| 231 | 6 | 150 | 4844 |
| 232 | 6 | 200 | 4794 |
| 233 | 6 | 250 | 4744 |
| 234 | 6 | 300 | 4694 |
| 235 | 6 | 400 | 4594 |
| 236 | 6 | 500 | 4494 |
| 237 | 12 | 25 | 4963 |
| 238 | 12 | 50 | 4938 |
| 239 | 12 | 100 | 4888 |
| 240 | 12 | 200 | 4788 |
| 241 | 12 | 300 | 4688 |
| 242 | 12 | 400 | 4588 |
| 243 | 12 | 500 | 4488 |
| 244 | 12 | 25 | 24963 |
| 245 | 12 | 300 | 24688 |
| 246 | 12 | 400 | 24588 |
| 247 | 12 | 500 | 24488 |
| 248 | 12 | 25 | 19963 |
| 249 | 12 | 300 | 19688 |
| 250 | 12 | 400 | 19588 |
| 251 | 12 | 500 | 19488 |
| 252 | 6 | 600 | 4394 |
| 253 | 6 | 800 | 4194 |
| 254 | 12 | 600 | 4388 |
| 255 | 12 | 800 | 4188 |
| 256 | 24 | 600 | 4376 |
| 257 | 24 | 800 | 4176 |
| 258 | 6 | 600 | 9394 |
| 259 | 6 | 800 | 9194 |
| 260 | 12 | 600 | 9388 |
| 261 | 12 | 800 | 9188 |
| 262 | 24 | 600 | 9376 |
| 263 | 24 | 800 | 9176 |
| 264 | 6 | 600 | 14394 |
| 265 | 6 | 800 | 14194 |
| 266 | 12 | 600 | 14388 |
| 267 | 12 | 800 | 14188 |
| 268 | 24 | 600 | 14376 |
| 269 | 24 | 800 | 14176 |
| 270 | 6 | 600 | 19394 |
| 271 | 6 | 800 | 19194 |
| 272 | 12 | 600 | 19388 |
| 273 | 12 | 800 | 19188 |
| 274 | 24 | 600 | 19376 |
| 275 | 24 | 800 | 19176 |
| 276 | 6 | 600 | 24394 |
| 277 | 6 | 800 | 24194 |
| 278 | 12 | 600 | 24388 |
| 279 | 12 | 800 | 24188 |
| 280 | 24 | 600 | 24376 |
| 281 | 24 | 800 | 24176 |

What is claimed is:

1. A medicament containing, separately or together, a synergistically effective amount of (A) formoterol or a pharmaceutically acceptable salt thereof or a solvate of formoterol or a solvate of said salt and (B) mometasone furoate, for simultaneous, sequential or separate administration in the treatment of an inflammatory or obstructive airways disease, wherein said (A) or (B), or (A) and (B) are in inhalable form in an atomizable composition or in a dry powder.

2. A medicament according to claim 1 which is a pharmaceutical composition comprising a mixture of synergistically effective amounts of (A) and (B), optionally together with a pharmaceutically acceptable carrier.

3. A medicament according to claim 1, in which (A) is formoterol fumarate dihydrate.

4. A medicament according to claim 2, in which (A) is formoterol fumarate dihydrate.

5. A medicament according to claim 1, which is an inhalable aerosol comprising a mixture of (A) and (B) in solution or dispersion in a propellant, or a combination of an aerosol containing (A) in solution or dispersion in a propellant with an aerosol containing (B) in solution or dispersion in a propellant.

6. A medicament according to claim 5, in which (A) or (B), or (A) and (B), are in dispersion in the propellant, which is a halogen-substituted hydrocarbon.

7. A medicament according to claim 6, in which (A) or (B), or each of (A) and (B), has an average particle diameter of up to 10 μm.

8. A medicament according to claim 1, which is an inhalable nebulizable composition comprising a dispersion of (A) and (B) in an aqueous, organic or aqueous/organic medium or a combination of a dispersion of (A) in said medium with a dispersion of (B) in said medium.

9. A medicament according to claim 1, which is an inhalable dry powder comprising finely divided (A) or (B), or finely divided (A) and (B), optionally together with a pharmaceutically acceptable earner in finely divided form.

10. A medicament according to claim 9, in which the carrier is present and is a saccharide.

11. A medicament according to claim 10, in which the carrier is lactose.

12. A medicament according to claim 9, in which (A) or (B), or each of (A) and (B), has an average particle diameter up to 10 urn.

13. A medicament according to claim 1, in which the weight ratio of (A) to (B) is from 2:1 to 1:2000.

14. A medicament according to claim 13, in which said ratio is from 1:5 to 1:50.

15. A medicament according to claim 2, in which the weight ratio of (A) to (B) is from 1:5 to 1:50.

16. A medicament according to claim 2, which is a dry powder in a capsule, the capsule containing from 3 to 36 μg of (A) as formoterol fumarate dihydrate, from 25 μg to 800 μg of (B) and a pharmaceutically acceptable carrier in an amount to bring the total weight of dry powder per capsule to between 5 mg and 50 mg.

17. A medicament according to claim 2, which is a dry powder comprising, by weight, from 3 to 36 parts of (A) as formoterol fumarate dihydrate, from 25 to 800 parts of (B) and 2164 to 24972 parts of a pharmaceutically acceptable carrier.

18. A method of treating an inflammatory or obstructive airways disease which comprises administering to a subject in need of such treatment a synergistically effective amount of (A) as defined in claim 1 and (B) as defined in claim 1.

19. A method of treating an inflammatory or obstructive airways disease which comprises administering to a subject in need of such treatment an effective amount of a medicament according to claim 2.

20. A pharmaceutical kit comprising (A) as defined in claim 1 and (B) as defined in claim 1 in separate unit dosage forms, said forms being suitable for administration of (A) and (B) in synergistically effective amounts, together with one or more inhalation devices for administration of (A) and (B).

* * * * *

UNITED STATES PATENT AND TRADEMARK OFFICE

CERTIFICATE OF CORRECTION

PATENT NO. : 7,566,705 B2
APPLICATION NO. : 11/199291
DATED : July 28, 2009
INVENTOR(S) : Hassan et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (68) days Delete the phrase "by 68 days" and insert -- by 145 days --

Signed and Sealed this

Seventeenth Day of August, 2010

David J. Kappos

David J. Kappos
*Director of the United States Patent and Trademark Office*